US009155559B2

(12) United States Patent
Ross et al.

(10) Patent No.: US 9,155,559 B2
(45) Date of Patent: *Oct. 13, 2015

(54) EXTERNAL FIXATOR STRUT

(71) Applicant: Texas Scottish Rite Hospital for Children, Dallas, TX (US)

(72) Inventors: John D. Ross, Dallas, TX (US); Mikhail L. Samchukov, Dallas, TX (US); Alexander M. Cherkashin, Dallas, TX (US); John G. Birch, Dallas, TX (US)

(73) Assignee: TEXAS SCOTTISH RITE HOSPITAL FOR CHILDREN, Dallas, TX (US)

( * ) Notice: Subject to any disclaimer, the term of this patent is extended or adjusted under 35 U.S.C. 154(b) by 300 days.

This patent is subject to a terminal disclaimer.

(21) Appl. No.: 13/891,382

(22) Filed: May 10, 2013

(65) Prior Publication Data

US 2013/0253513 A1 Sep. 26, 2013

Related U.S. Application Data

(63) Continuation of application No. 12/864,807, filed as application No. PCT/US2009/033603 on Feb. 9, 2009, now Pat. No. 8,439,914.

(60) Provisional application No. 61/027,408, filed on Feb. 8, 2008.

(51) Int. Cl.
*A61B 17/64* (2006.01)
*A61B 17/62* (2006.01)

(52) U.S. Cl.
CPC ............... *A61B 17/62* (2013.01); *A61B 17/64* (2013.01)

(58) Field of Classification Search
CPC ........ A61B 17/58; A61B 17/60; A61B 17/62; A61B 17/64–17/6491

USPC ...................................................... 606/53–59
See application file for complete search history.

(56) References Cited

U.S. PATENT DOCUMENTS 2,238,870 A 4/1941 Haynes
2,346,346 A 4/1944 Anderson
(Continued)

FOREIGN PATENT DOCUMENTS

CA 2633944 A1 7/2007
DE 3802743 A1 8/1989
(Continued)

OTHER PUBLICATIONS

European Extended Search Report, EP Application No. 09710983.9-1654 / 2249721 PCT/US2009/033975, dated Apr. 4, 2014, 7 pages.
(Continued)

*Primary Examiner* — Jerry Cumberledge
*Assistant Examiner* — Nicholas Plionis
(74) *Attorney, Agent, or Firm* — Baker & McKenzie LLP

(57) ABSTRACT

The present disclosure provides an external fixation strut for an external fixation device having a ball joints that can be attached to the outer or inner surface of the ring and locked to increase overall stability of the external fixation device. Some embodiments of the fixation strut include a first ball joint coupled to a first end portion of a strut housing, the strut housing having an axial bore defined therethrough. A second ball joint is coupled to a second end portion of an elongated member. The elongated member is coupled to an adjustment mechanism, which is coupled to an upper end portion of an adjustment sleeve. The adjustment sleeve is slidably disposed in the axial bore of the strut housing, and is used to effect coarse strut length adjustments. Gradual strut adjustments are effected by translating the elongated member.

22 Claims, 9 Drawing Sheets

(56) References Cited

U.S. PATENT DOCUMENTS

| | | | |
|---|---|---|---|
| 4,308,863 | A | 1/1982 | Fischer |
| 4,365,624 | A | 12/1982 | Jaquet |
| 4,621,627 | A | 11/1986 | DeBastiani et al. |
| 4,768,524 | A | 9/1988 | Hardy |
| 4,889,111 | A | 12/1989 | Ben-Dov |
| 4,973,331 | A | 11/1990 | Pursley et al. |
| 4,988,244 | A | 1/1991 | Sheldon et al. |
| 5,019,077 | A | 5/1991 | De Bastiani et al. |
| 5,095,919 | A | 3/1992 | Monticelli et al. |
| 5,156,605 | A | 10/1992 | Pursley et al. |
| 5,180,380 | A | 1/1993 | Pursley et al. |
| 5,458,599 | A | 10/1995 | Adobbati |
| 5,533,418 | A | 7/1996 | Wu et al. |
| 5,702,389 | A | 12/1997 | Taylor et al. |
| 5,728,095 | A | 3/1998 | Taylor et al. |
| 5,776,132 | A | 7/1998 | Blyakher |
| 5,863,292 | A | 1/1999 | Tosic |
| 5,885,283 | A | 3/1999 | Gittleman |
| 5,891,143 | A | 4/1999 | Taylor et al. |
| 5,928,230 | A | 7/1999 | Tosic |
| 5,971,984 | A | 10/1999 | Taylor et al. |
| 6,030,386 | A | 2/2000 | Taylor et al. |
| 7,282,052 | B2 | 10/2007 | Mullaney |
| RE40,914 | E | 9/2009 | Taylor et al. |
| 8,029,505 | B2 | 10/2011 | Hearn et al. |
| 8,202,273 | B2 | 6/2012 | Karidis |
| 8,257,353 | B2 | 9/2012 | Wong |
| 8,296,094 | B2 | 10/2012 | Harrison et al. |
| 8,333,766 | B2 | 12/2012 | Edelhauser et al. |
| 8,366,710 | B2 | 2/2013 | Hirata et al. |
| 8,377,060 | B2 | 2/2013 | Vasta et al. |
| 8,388,619 | B2 | 3/2013 | Mullaney |
| 2002/0010465 | A1 | 1/2002 | Koo et al. |
| 2003/0149378 | A1 | 8/2003 | Peabody et al. |
| 2003/0191466 | A1 | 10/2003 | Austin et al. |
| 2003/0199856 | A1 | 10/2003 | Hill et al. |
| 2003/0212398 | A1 | 11/2003 | Jackson |
| 2004/0073211 | A1 | 4/2004 | Austin et al. |
| 2004/0097922 | A1 | 5/2004 | Mullaney |
| 2004/0116926 | A1 | 6/2004 | Venturini et al. |
| 2005/0192572 | A1 | 9/2005 | Abdelgany et al. |
| 2005/0215997 | A1 | 9/2005 | Austin et al. |
| 2005/0234457 | A1 | 10/2005 | James et al. |
| 2006/0052782 | A1 | 3/2006 | Morgan et al. |
| 2006/0207118 | A1 | 9/2006 | Kim |
| 2006/0235389 | A1 | 10/2006 | Albert et al. |
| 2007/0055234 | A1 | 3/2007 | McGrath et al. |
| 2007/0055254 | A1 | 3/2007 | Ihde |
| 2007/0083087 | A1 | 4/2007 | Carda |
| 2007/0085496 | A1 | 4/2007 | Philipp et al. |
| 2007/0225704 | A1 | 9/2007 | Ziran et al. |
| 2007/0233134 | A1 | 10/2007 | Bastian et al. |
| 2008/0021451 | A1 | 1/2008 | Coull et al. |
| 2009/0036890 | A1 | 2/2009 | Karidis |
| 2009/0036892 | A1 | 2/2009 | Karidis et al. |
| 2010/0087819 | A1 | 4/2010 | Mullaney |
| 2010/0262160 | A1 | 10/2010 | Boyden et al. |
| 2010/0262239 | A1 | 10/2010 | Boyden et al. |
| 2010/0305568 | A1 | 12/2010 | Ross et al. |
| 2010/0312243 | A1 | 12/2010 | Ross et al. |
| 2010/0331840 | A1 | 12/2010 | Ross et al. |
| 2011/0004199 | A1 | 1/2011 | Ross et al. |
| 2011/0118738 | A1 | 5/2011 | Vasta et al. |
| 2011/0166572 | A1 | 7/2011 | Ihde |
| 2011/0313418 | A1 | 12/2011 | Nikonovas |
| 2011/0313419 | A1 | 12/2011 | Mullaney |
| 2012/0041439 | A1 | 2/2012 | Singh et al. |
| 2012/0130384 | A1 | 5/2012 | Henderson |
| 2012/0303028 | A1 | 11/2012 | Wong |
| 2012/0303029 | A1 | 11/2012 | Vasta et al. |
| 2013/0018374 | A1 | 1/2013 | Edelhauser et al. |

FOREIGN PATENT DOCUMENTS

| | | | |
|---|---|---|---|
| DE | 9316164 | U1 | 7/1994 |
| DE | 4421223 | A1 | 12/1995 |
| DE | 102007026404 | A1 | 12/2008 |
| EP | 0029298 | A1 | 5/1981 |
| EP | 1239784 | B1 | 4/2006 |
| EP | 1916952 | B1 | 12/2009 |
| EP | 2134515 | B1 | 7/2010 |
| EP | 2417923 | A1 | 2/2012 |
| GB | 421788 | | 12/1934 |
| GB | 2229096 | A | 9/1990 |
| IT | 1259768 | B | 3/1996 |
| JP | S52-003290 | | 8/1978 |
| JP | S63-500499 | | 2/1988 |
| JP | H02180254 | A | 7/1990 |
| JP | H10290807 | A | 11/1998 |
| JP | 2003508108 | A | 3/2003 |
| JP | 2003508150 | A | 3/2003 |
| JP | 2005137586 | A | 6/2005 |
| WO | 9222268 | A1 | 12/1992 |
| WO | 9626678 | A1 | 9/1996 |
| WO | 9730650 | A1 | 8/1997 |
| WO | 9812975 | A2 | 4/1998 |
| WO | 9815231 | A1 | 4/1998 |
| WO | 9920193 | A1 | 4/1999 |
| WO | 9947060 | A1 | 9/1999 |
| WO | 9948414 | A2 | 9/1999 |
| WO | 0003647 | A1 | 1/2000 |
| WO | 0115611 | A1 | 3/2001 |
| WO | 0122892 | A1 | 4/2001 |
| WO | 03086211 | A1 | 10/2003 |
| WO | 03086212 | A2 | 10/2003 |
| WO | 03086213 | A2 | 10/2003 |
| WO | 2004026103 | A2 | 4/2004 |
| WO | 2007002180 | A2 | 1/2007 |
| WO | 2007060507 | A2 | 5/2007 |
| WO | 2007139031 | A1 | 12/2007 |
| WO | 2008002992 | A1 | 1/2008 |
| WO | 2008134624 | A1 | 11/2008 |
| WO | 2009018349 | A2 | 2/2009 |
| WO | 2009018398 | A2 | 2/2009 |
| WO | 2009100247 | A1 | 8/2009 |
| WO | 2009100459 | A1 | 8/2009 |
| WO | 2009102904 | A1 | 8/2009 |
| WO | 2009105479 | A1 | 8/2009 |
| WO | 2010042619 | A1 | 4/2010 |
| WO | 2010104567 | A1 | 9/2010 |
| WO | 2010120367 | A1 | 10/2010 |
| WO | 2011017321 | A2 | 2/2011 |
| WO | 2011060264 | A1 | 5/2011 |
| WO | 2011060266 | A1 | 5/2011 |
| WO | 2011106507 | A1 | 9/2011 |
| WO | 2011146703 | A1 | 11/2011 |
| WO | 2011163406 | A2 | 12/2011 |

OTHER PUBLICATIONS

International Search Report, PCT/US2009/034413, dated Apr. 15, 2009, 1 page.
International Preliminary Report on Patentability, PCT/US2009/034413, dated Aug. 24, 2010, 7 pages.
Extended European Search Report, Application No. 09712412.7-1526, PCT/US2009/034413, dated Dec. 3, 2012, 10 pages.
International Search Report, PCT/US2010/056541, dated Jan. 12, 2011, 1 page.
International Preliminary Report on Patentability, PCT/US2010/056541, Date of issuance May 15, 2012, 7 pages.
International Preliminary Report on Patentability, PCT/US2010/056539, Date of issuance May 15, 2012, 9 pages.
International Search Report, PCT/US2010/056539, Dated Jan. 18, 2011, 2 pages.
Steffen Schumann, et al., "Calibration of X-ray radiographs and its feasible application for 2D/3D reconstruction of the proximal femur" (2008), 4 pages.
Jetzki S., et al., "Fluoroscopy-Based 3-D Reconstruction of Femoral Bone Cement: A New Approach for Revision Total Hip Replacement," (2005), 12 pages.

(56) References Cited

OTHER PUBLICATIONS

Guoyan Zheng, et al., "3-D reconstruction of a surface model of the proximal femur from digital biplanar radiographs," (2008), 4 pages.
Laporte S., et al., "A biplanar reconstruction method based on 2D and 3D contours: application to the distal femur," (2003), 6 pages.
Japanese Office Action, JP Application No. 2010-546960, dated Mar. 12, 2013, 4 pages.
Japanese Office Action, JP Application No. 2010-546904, dated Mar. 12, 2013, 6 pages.
Japanese Office Action, JP Application No. 2010-546098, dated Mar. 5, 2013, 11 pages.
International Preliminary Report on Patentability, PCT/RU2010/000452, dated Feb. 26, 2013, 9 pages.
Japanese Office Action, JP Application No. 2010-545284, dated Mar. 5, 2013, 6 pages.
Japanese Office Action, dated Nov. 26, 2013, JP Application No. 2010-545284, 4 pages.
Extended European Search Report, EP 09708841.3-1654 / 2240085; PCT/US2009/033603, dated Dec. 2, 2013, 5 pages.
European Extended Search Report, Application No. 09707791.1-1654 / 2240084, PCT/US2009/033258, dated Nov. 21, 2013, 6 pages.
Japanese office action, JP Application No. 2010-546904, dated Oct. 29, 2013, 4 pages.
International Search Report and Written Opinion, PCT/US2013/064067, dated Jan. 31, 2014, 7 pages.
International Search Report and Written Opinion, PCT/RU2013/000203, dated Jan. 29, 2014, 23 pages.
Canero, C., et al., "Predictive (Un)distortion Model and 3-D Reconstruction by Biplane Snakes, IEEE Transactions on Medical Imaging," vol. 21, No. 9, (Sep. 2002), 14 pages.
Ghanem, R.N., et al., "Heart-Surface Reconstruction and ECG Electrodes Localization Using Fluoroscopy, Epipolar Geometry and Stereovision: Application to Noninvasive Imaging of Cardiac Electrical Activity," IEEE Transactions on Medical Imaging, vol. 22, No. 10, (Oct. 2003), 12 pages.
Li, Y., et al., "Distortion Correction and Geometric Calibration for X-Ray Angiography System," IEEE Transactions on Nuclear Science, vol. 56, No. 3, (Jun. 2009), 12 pages.
Selby, B.P., et al., "Patient positioning with X-ray detector self-calibration for image guided therapy," Australas Phys. Eng. Sci. Med., vol. 34, (2011), 10 pages.
Yang, J., et al., "Novel Approach for 3-D Reconstruction of Coronary Arteries From Two Uncalibrated Angiographic Images," IEEE Transactions on Image Processing, vol. 18, No. 7, (Jul. 2009), 10 pages.
Zheng, G., et al., "A 2D/3D correspondence building method for reconstruction of a patient-specific 3D bone surface model using point distribution models and calibrated X-ray images," Medical Image Analysis, vol. 13, (2009), 17 pages.

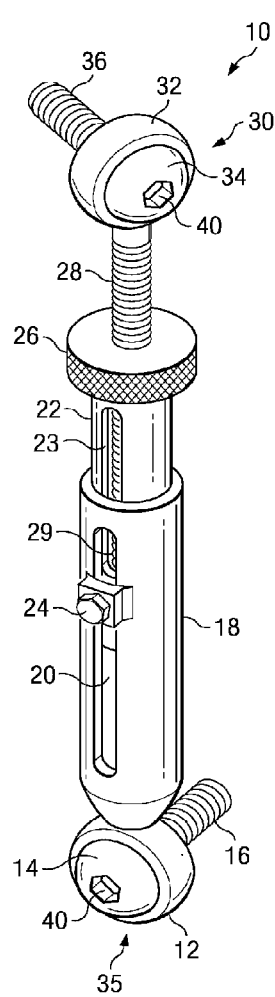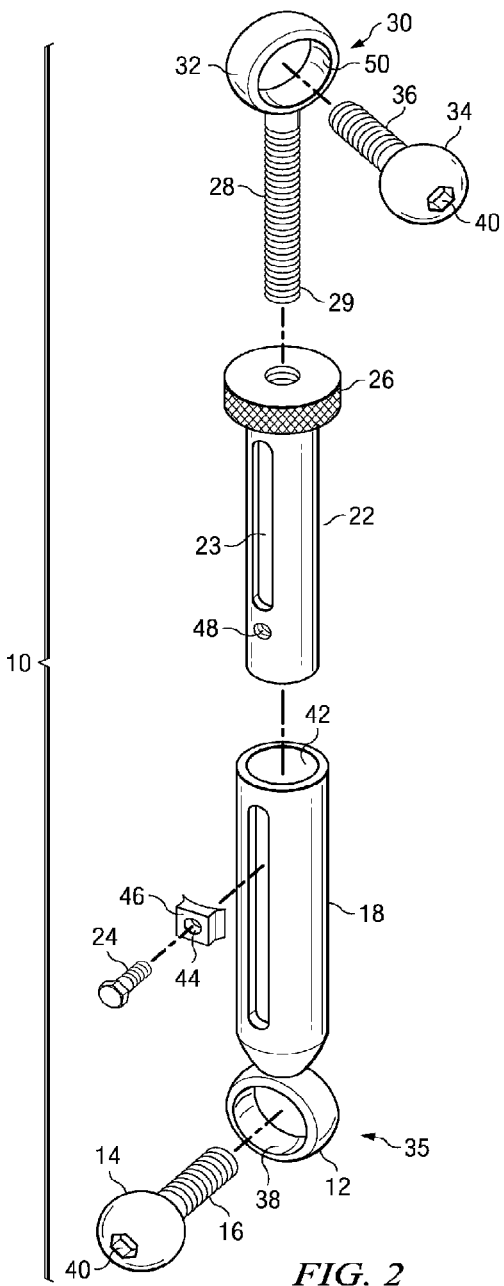
FIG. 1
FIG. 2

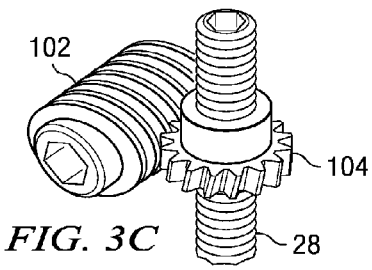
FIG. 3C
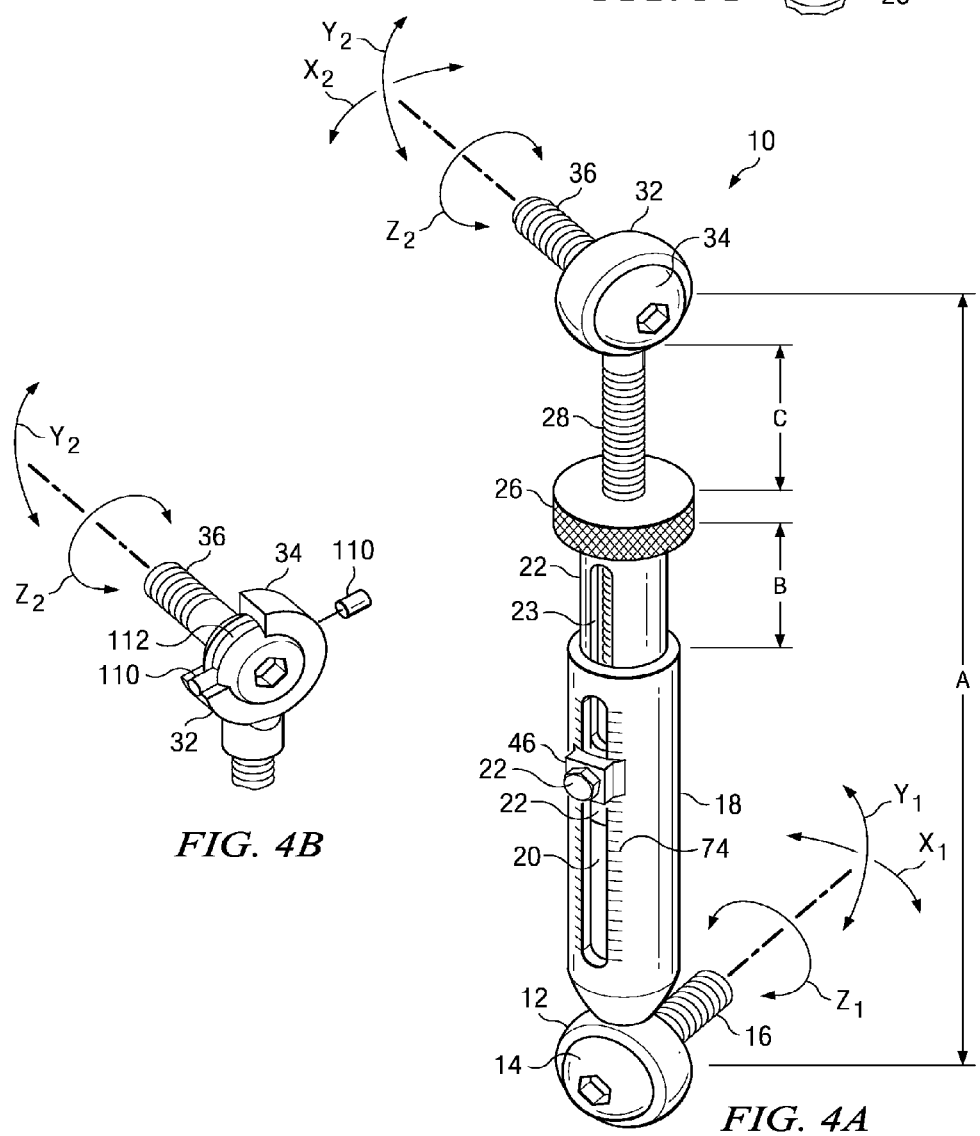
FIG. 4B
FIG. 4A

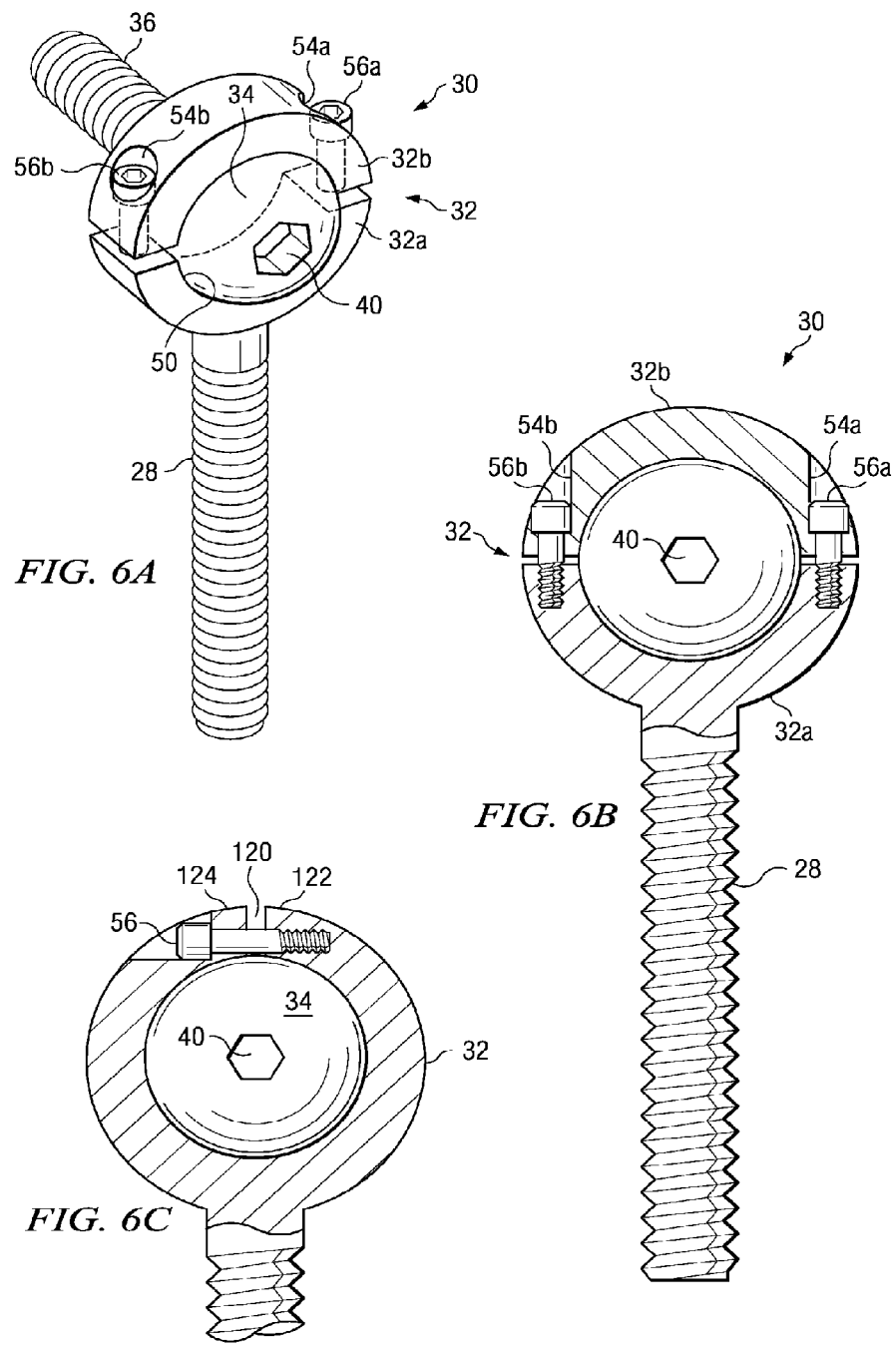

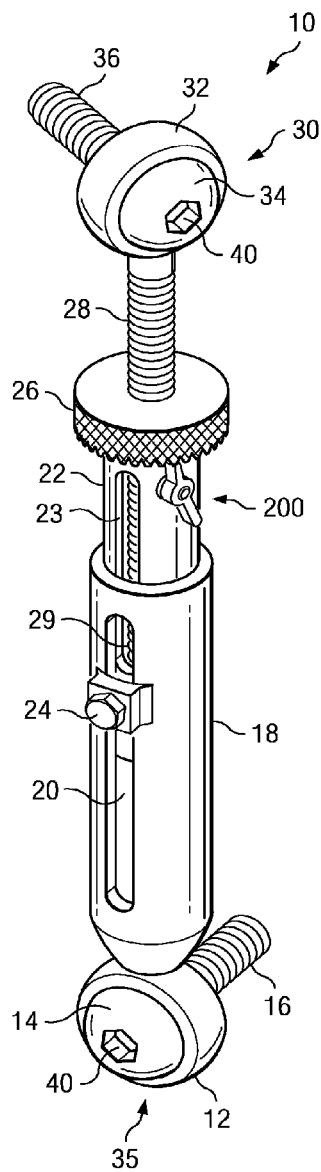
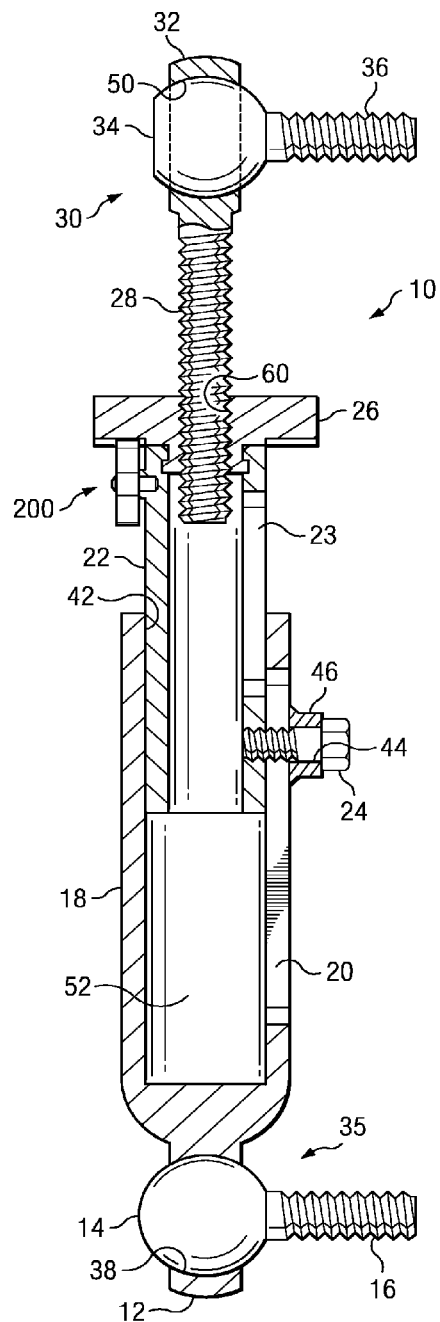
FIG. 12A
FIG. 12B

EXTERNAL FIXATOR STRUT

CROSS-REFERENCE TO RELATED APPLICATIONS

This patent application is a continuation application of U.S. application Ser. No. 12/864,807, filed on Jul. 27, 2010, which is a national phase filing under section 371 of PCT/US2009/033603, filed Feb. 9, 2009, which claims the priority of U.S. Provisional Application 61/027,408, filed Feb. 8, 2008, each of which is incorporated herein by reference in its entirety.

TECHNICAL FIELD

The present disclosure relates in general to the field of external fixation, and more specifically, to external fixator connection struts and other connection rods.

BACKGROUND

Without limiting the scope of the disclosure, this background is described in connection with external fixation devices and specifically connection struts and rods. Generally, external fixation devices are commonly used in a variety of surgical procedures including limb lengthening and deformity correction. The process involves a rigid framework comprising several rings that are placed externally around the limb and attached to bone segments using wires and half pins inserted into the bone segments and connected to the related section of the external rigid framework. The opposite rings of the rigid framework are interconnected by either threaded or telescopic rods directly or in conjunction with uni-planar or multi-planar hinges, which allows the surgeon to adjust position of the rings relative to each other longitudinally, rotationally, horizontally or angularly over a period of time.

For example, in limb lengthening, the bone is surgically divided into two segments and wires and half pins are inserted into bone segments above and below the surgical bone cut and attached to rings of a rigid framework interconnected by struts or telescopic connection rods. The rigid framework is used to gradually push the two bone segments apart longitudinally over a period of time (e.g., one millimeter a day). This allows the bone to gradually form in the gap between bone segments created by this distraction technique. Once the desired amount of lengthening is achieved (e.g., 5-6 cm), the external apparatus is stabilized into a fixed position and left on the bone segments until complete mineralization of the newly formed bone (e.g., 3-6 months, depending on the nature of pathology and amount of lengthening).

Similarly, in deformity correction, the bone is surgically divided (usually at the apex of the deformity) into two segments and wires and half pins are inserted into bone segments above and below the surgical bone cut and attached to rings of a rigid framework. Opposite rings of the rigid framework are connected together by threaded rods with attached uni-planar or multi-planar hinges and angular distractor that is used to gradually push the two bone segments apart angularly over a period of time.

One common fixation device is a circular metal structure known as the Ilizarov Apparatus. The Ilizarov apparatus, when used for limb lengthening or deformity correction, consists of several rings or arches that are placed externally around the limb and attached to surgically separated bone segments using wires and half pins. For limb lengthening, the opposite rings are interconnected directly by three or four threaded or telescopic rods that are regularly adjusted in length and allowed for gradual separation of bone segments longitudinally. For angular deformity correction, the opposite rings of the Ilizarov apparatus are connected by a pair of hinges that provide an axis of rotation for bone segments and an angular distractor that gradually pushes two rings and associated bone segments apart.

Another common external fixation device is the Taylor Spatial Frame, which is a hexapod type external fixation device based on a Stewart platform but shares many components and features of the Ilizarov apparatus. The Taylor Spatial Frame consists of two external fixation rings attached to bone segments by wires and half pins and connected together by 6 telescopic struts with multi-planar hinges located at both ends of the strut. Each strut may be lengthened or shortened as necessary to either pull two interconnected ring segments towards each other or push them apart. Adjustment of strut length allows manipulating with bone segments acutely or gradually in 6 axes (e.g., lengthening/shortening external/internal rotation, anterior/posterior horizontal translation, medial/lateral horizontal translation, anterior/posterior angular translation, and medial/lateral angular translation) to perform limb lengthening and correct angular, translational and rotational deformities simultaneously.

The Taylor Spatial Frame includes a plurality of struts interconnecting a pair of rings. The wires, half pins, struts and other connection and assembly elements of the frame are connected to the rings via apertures defined therein. All of those apertures or holes are located on the same ring surfaces extending through the upper ring surface to the lower ring surface. This creates a positioning problem for wire and half pin attachment and placement of the additional connection rods and assembly elements due to the competition for holes in the fixation ring of the frame or the wires and pins interfering with the connections of the struts to the holes.

Each strut of the Taylor Spatial Frame has a threaded rod partially disposed inside of a hollow shaft, and the hollow shaft includes an adjustment nut that mates with the threaded rod. To effect either a coarse adjustment (rapid strut length adjustment) or a fine adjustment (gradual strut length adjustment) to the length of the strut, the same threaded rod is pulled out or pushed in relative to the hollow shaft. Because the threaded rod has a finite length, however, using the same threaded rod for rapid strut length adjustment limits the total amount of threaded rod available for gradual strut length adjustment during, for example, limb lengthening and deformity correction. As a result, a time consuming exchange of the struts for longer ones during the treatment is required.

Additionally, the replacement or removal of a strut from the Taylor Spatial Frame during the course of treatment is impossible without using external support or other stabilization mechanism to support the rest of frame. The struts of the Taylor Spatial Frame are required to be connected at the top or bottom of the rings. Such connections require the use of either ball joints in the holes of the rings or universal joints extending from the top or bottom surfaces of the rings. The Taylor Spatial Frame, however, does not include any locking mechanism for temporarily locking the universal joints or ball joints in their orientation. As a result, if one strut is removed from the frame, it would become unstable and collapse.

The universal joints and ball joints of the Taylor Spatial Frame also make strut length adjustments inaccurate and inconvenient. The joints of the Taylor Spatial Frame allow each strut to have three degrees of rotational freedom, including an undesirable degree of freedom for axial rotation. As such, when the adjustment nut of a strut is rotated axially to effect a strut length adjustment as discussed above, the entire strut would also rotate axially, thereby keeping the threaded rod of the strut from translating relative to the hollow shaft of the strut. To allow the threaded rod to translate as desired, one would have to use a second hand or a vice to secure the hollow shaft from axial rotation. Absent such an inconvenient step, strut length adjustments would be inaccurate.

Both types of joints have additional drawbacks. One drawback for using ball joints is that there is insufficient spatial clearance for the ball joints to effect some adjustments to the orientation of the struts and the rings. A drawback for using universal joints is the decrease in the functional length of the struts due to the space taken up by the length of the universal joints. Another drawback is the instability caused by universal joints. The universal joints each include at least one hinge connection, in which a pivot pin is commonly and loosely held by two rotating parts that are designed to rotate about the longitudinal axis defined by the pivoting pin. Due to the loose coupling between the rotating parts and the pivoting pin, a degree of undesirable translational movement is inherent in the design of the hinge connection and introduces instability to the Taylor Spatial Frame.

SUMMARY

Various embodiments of an improved external fixation strut is included in this disclosure. In one embodiment, the external fixation strut includes a strut housing having an axial bore defined therethrough, a first ball joint coupled to an end portion of the strut housing, and an adjustment sleeve slidably disposed within the axial bore, the adjustment sleeve and the strut housing being releasably coupled by a connector. The external fixation strut further includes an externally threaded elongated member, a second ball joint coupled to an end portion of the threaded elongated member, and an adjustment mechanism comprising a rotation element. The rotation element has an internally threaded bore defined therethrough, wherein the threaded elongated member is disposed through the threaded bore, the external thread of the elongated member and the internal thread of the threaded bore mating with each other such that rotating the rotation element would cause the threaded elongated member to translate. The adjustment mechanism is rotatably coupled to an end portion of the adjustment sleeve, and the adjustment mechanism is operable to rotate but not translate relative to adjustment sleeve.

Also included in the present disclosure are various embodiments for a method of interconnecting first and second fixator rings with a strut, adjusting the strut to a pretreatment strut length, and making desired strut length adjustments during treatment. The rings each comprising a plurality of apertures defined in the inner or outer side surface of the ring. In one embodiment, the disclosed method comprises providing a first part of a strut comprising a first ball joint coupled to an end portion of a strut housing, the strut housing having an axial bore defined therethrough, the first ball joint comprising a first ball stud. The method further includes providing a second part of the strut. The second part includes a second ball joint coupled to an end portion of a threaded elongated member, the threaded elongated member being threadably coupled to an adjustment mechanism, wherein the adjustment mechanism is rotatably coupled to an end portion of an adjustment sleeve, the adjustment mechanism being operable to rotate but not translate relative to the adjustment sleeve. The second ball joints comprises a second ball stud. The method further includes slidably disposing the adjustment sleeve within the axial bore of the strut housing. The method further includes connecting the ball stud of the first ball joint to a first aperture of the first ring, and connecting the ball stud of the second ball joint to a second aperture of the second ring. Other steps included in the disclosed embodiment of the method include positioning the adjustment sleeve relative to the strut housing to arrive at the pretreatment strut length, and releasably coupling the adjustment sleeve to the strut housing.

BRIEF DESCRIPTION OF THE DRAWINGS

For a more complete understanding of the features and advantages of the present disclosure, reference is now made to the detailed description of the disclosure along with the accompanying figures and in which:

FIG. 1 is a perspective view of one embodiment of an external fixation strut of the present disclosure.

FIG. 2 is an exploded view of the external fixation strut of FIG. 1.

FIG. 3C is a focused, cutaway view of the external fixation strut of FIG. 3B.

FIG. 4A is a perspective view of a embodiment of the external fixation strut of the present disclosure.

FIG. 4B is a perspective view of a portion of the external fixation strut shown in FIG. 4A.

FIG. 6A is a perspective and cutaway view of a ball joint lockable by a split ball joint cage.

FIG. 6B is a perspective and cutaway view of the ball joint of FIG. 6A.

FIG. 6C is a perspective and cutaway view of another ball joint lockable by a split ball joint cage.

FIG. 12A is a perspective view of an embodiment of an external fixation strut of the present disclosure.

FIG. 12B is a cutaway view of an embodiment of an external fixation strut of the present disclosure.

DETAILED DESCRIPTION

Figure 3A:
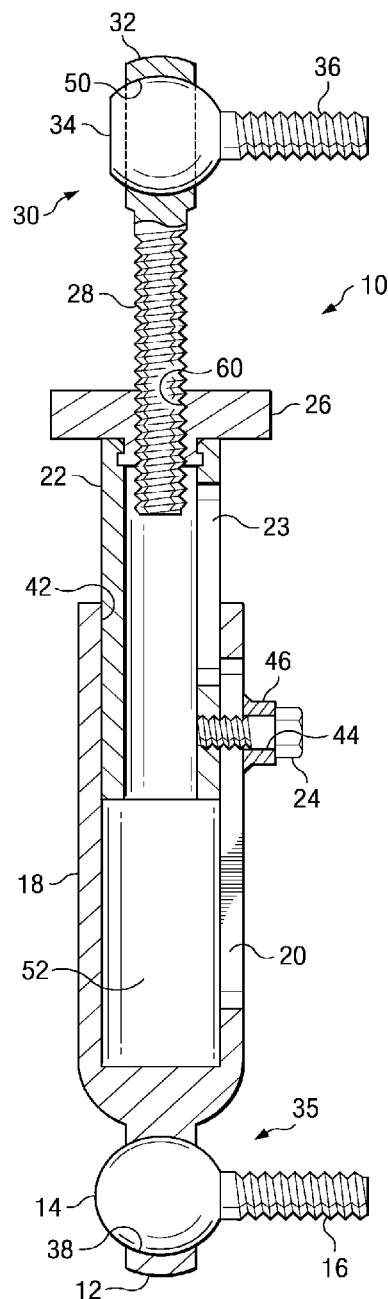
FIG. 3A is a cutaway view of one embodiment of an external fixation strut of the present disclosure.

While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not delimit the scope of the disclosure.

To facilitate the understanding of this disclosure, a number of terms are defined below. Terms defined herein have meanings as commonly understood by a person of ordinary skill in the areas relevant to the present disclosure. Terms such as "a", "an" and "the" are not intended to refer to only a singular entity, but include the general class of which a specific example may be used for illustration. The terminology herein is used to describe specific embodiments of the disclosure, but their usage does not delimit the disclosure, except as outlined in the claims.

The present disclosure provides an external fixation strut having ball joints that can be attached to the outer or inner surface of a fixation ring and housing that allows for independent rapid and gradual adjustment in length. The external fixation strut includes a first ball joint having a first ball stud extending from a first ball member that is at least partially surrounded by a first ball cage. The first ball stud attaches to an aperture in an outer or inner surface of the external fixator ring or other external support. The external fixation strut includes a strut housing comprising an axial bore extending longitudinally from the ball cage and an adjustment sleeve slidably fitted within the axial bore of the strut housing and a sleeve fastener positioned to secure the adjustment sleeve to the strut housing. The adjustment sleeve adjusts coarse rapid longitudinal movement with respect to the strut housing and an adjustment mechanism positioned at one end of the adjustment sleeve and threadably connected to a threaded elongated member. The adjustment mechanism gradually adjusts longitudinally the threaded elongated member and a second ball joint connected to the threaded elongated member. The second ball joint includes a second ball stud extending from a second ball member that is at least partially surrounded by a second ball cage. The second ball stud attaches to an aperture in an outer or inner surface of the external fixator ring or other external support.

FIG. 1 is a perspective view of one embodiment of the external fixation strut of the present disclosure for an external fixation device. The external fixation strut 10 includes a first ball joint cage 12 that at least partially encloses a first ball member 14 that includes a first ball stud 16 that is operable to be received in an aperture of an external fixator ring or other external support (not shown) to secure the first ball member 14 of the first ball joint cage 12 to an external fixator ring or other external support (not shown).

A telescoping strut housing 18 extends from the first ball joint cage 12 and has an aperture (not shown) extending longitudinally from the first ball joint cage 12. The first ball joint cage 12 allows angular and rotational alignment of the telescoping strut housing 18 relative to the first ball member 14. The telescoping strut housing 18 includes a telescoping housing adjustment aperture 20. An adjustment sleeve 22 is slidably disposed in the axial bore (not shown) of the telescoping strut housing 18. The adjustment sleeve 22 is slidable within the axial bore (not shown) to allow adjustment of the coarse end-to-end length of the external fixation strut 10 in a rapid manner. The adjustment sleeve 22 includes a sleeve fastener 24 positioned through the telescoping housing adjustment aperture 20 to secure the adjustment sleeve 22 to the telescoping strut housing 18. In some embodiments, the adjustment aperture 20 may include preset holes for rapid longitudinal movement of the adjustment sleeve on the preset amount (e.g., 5 mm) relative to the strut housing. In these embodiments, the sleeve fastener 24 can be configured to have a neck portion that correspond to the shape of the preset holes for positive mechanical interference. As such, the coarse strut length adjustment does not involve translating the elongated member 28 relative to the adjustment sleeve 22, and the entire length of the elongated member 28 is preserved for gradual strut length adjustment as discussed below An adjustment mechanism 26 is rotatably coupled to an end portion of the adjustment sleeve 22 and threadably connected to the threaded elongated member 28. As such, the adjustment mechanism 26 is operable to rotate but not translate relative to the adjustment sleeve 22. The adjustment mechanism 26 generally includes a rotation element having a threaded bore defined therethrough, and the threaded elongated member 28 is disposed through the threaded bore. The threads of the threaded bore and the threaded elongated member 28 mate with each other, allowing the rotation of the rotation element to result in the longitudinal translation of the elongated member 28.

In the embodiments shown in FIG. 1, the adjustment mechanism 26 includes a thumbwheel seated in a groove portion (not shown) defined in an upper end portion the adjustment sleeve 22. The thumbwheel of the adjustment mechanism 26 is gradually rotated to translate the threaded elongated member 28 and to adjust the overall end-to-end length of the external fixation strut 10 in a gradual manner. The adjustment sleeve 22 includes a slot 23, through which one can observe the longitudinal position of an end portion 29 of the threaded elongated member 28 relative to the adjustment sleeve 22. As such, one can determine the amount longitudinal adjustment that was made. Although not shown in FIG. 1, it is to be appreciated that in some embodiments, the adjustment mechanism 26 may incorporate any security mechanism known in the art to limit the rotation of the thumbwheel in one or both directions so that the doctor or patient would not accidentally adjust the strut length. In one exemplary embodiment shown in FIGS. 12A and 12B, the adjustment mechanism 26 may include a ratchet-based locking mechanism 200 that can be engaged or disengaged by the push of a button or lever.

The threaded elongated member 28 includes a second ball joint 30 that includes a second ball joint cage 32 adapted to at least partially enclose a second ball member 34 having a second ball stud 36, which is operable to be received in an aperture in an external fixator ring or other external support (not shown). The skilled artisan will readily understand that the first and second ball members as well as the first and second ball studs may have one or more additional slots 40 or nuts (not shown) operably connected thereto to tighten and lock the ball or ball stud in the desired positions. The slots 40 may use any type head fastener known to the skilled artisan, e.g., slotted, Phillips, hex, socket, high-torque or other fastener/head.

FIG. 2 is an exploded view of one embodiment of the external fixation strut of the present disclosure for an external fixation device. The external fixation strut 10 includes a first ball joint cage 12 that at least partially encloses a first ball member 14. The first ball member 14 passes through a ball aperture 38 that is sized and proportioned to fit the first ball member 14. A first ball stud 16 is operable to secure the first ball member 14 to an external fixator ring or other external supports (not shown). The first ball joint cage 12 allows angular and rotational alignment of the external fixation strut 10 relative to the first ball member 14.

A telescoping strut housing 18 extends from the first ball joint cage 12 and has an axial bore extending longitudinally from the first ball joint cage 12 to the axial bore aperture 42. The telescoping strut housing 18 includes a telescoping housing adjustment aperture 20 defined in a wall of the strut housing 18. An adjustment sleeve 22 passes through the axial bore aperture 42 and is positioned in the axial bore of the telescoping strut housing 18. The adjustment sleeve 22 is slidable within the axial bore (not shown) to allow adjustment of the coarse end-to-end length of the connecting rod 10 in a rapid manner. The adjustment sleeve 22 includes a sleeve fastener 24 that is inserted through an aperture 44 centrally defined in a sleeve fastener washer 46 and through the telescoping housing adjustment aperture 20 into a sleeve fastener aperture 48 in the adjustment sleeve 22. In the embodiment shown in FIG. 2, the sleeve fastener aperture is a threaded radial bore defined in an end portion of the adjustment sleeve. The sleeve fastener washer 46 can have a variety of configurations to provide various design advantages. In some embodiments, the sleeve fastener washer 46 has a smooth inner surface (not shown). In some other embodiments, the inner surface of the sleeve fastener washer 46 has a teethed portion (not shown) cooperating with a matching teethed portion (not shown) of the telescoping strut housing 18 to provide a more secured connection with the strut housing 18.

An adjustment mechanism 26 is rotatably coupled to an end portion of the adjustment sleeve 22 and threadably connected to a threaded elongated member 28. The adjustment mechanism 26 adjusts longitudinally the threaded elongated member 28 to adjust the overall end-to-end length of the connecting rod 10 in a gradual manner. The adjustment sleeve 22 includes a slot 23, through which one can observe the longitudinal position of an end portion 29 of the threaded elongated member 28 relative to the adjustment sleeve 22. As such, one can determine the amount longitudinal adjustment that was made.

The threaded elongated member 28 includes a second ball joint 30. The second ball joint 30 includes a second ball joint cage 32 adapted to fit a second ball member 34. The second ball member 34 is fitted to a ball aperture 50 of the second ball cage 32 that is sized and proportioned to fit the second ball member 34. A second ball stud 36 is operable to be received in an aperture (not shown) in an external fixator ring or other external supports (not shown). The second ball joint cage 32 allows angular and rotational alignment of the external fixation strut 10 relative to the second ball member 34. The skilled artisan will readily understand that the first and second ball studs as well as the first and second ball members may have one or more additional slots 40 or nuts (not shown) operably connected thereto to tighten and lock the stud or ball in the desired positions. The slots 40 may use any type head fastener known to the skilled artisan, e.g., slotted, Phillips, hex, socket, high-torque or other fastener/head.

FIG. 3A is a cutaway view of one embodiment of the external fixation strut of the present disclosure for an external fixation device. The external fixation strut 10 includes a first ball joint cage 12 that houses a first ball member 14. The first ball member 14 passes through a first ball aperture 38 that is sized and proportioned to fit the first ball member 14. A first ball stud 16 is operable to be received in an aperture (not shown) in an external fixation ring or other external supports (not shown) to secure the first ball member 14 to an external fixator ring or other external supports (not shown). The first ball joint cage 12 allows angular and rotational alignment of the external fixation strut 10 relative to the first ball member 14.

A telescoping strut housing 18 extends from the first ball joint cage 12 and has an aperture 58 extending longitudinally from the first ball joint cage 12 to the axial bore aperture 42. The telescoping strut housing 18 includes a telescoping housing adjustment aperture 20 defined in a wall of the. An adjustment sleeve 22 passes through the axial bore aperture 42 and is positioned in the axial bore 58 of the telescoping strut housing 18. The adjustment sleeve 22 is slidable within the axial bore 58 to allow adjustment of the coarse end-to-end length of the connecting rod 10 in a rapid manner. The adjustment sleeve 22 includes a sleeve fastener 24 that is disposed through an aperture 44 of the sleeve fastener washer 46 and through the telescoping housing adjustment aperture (not shown) into a threaded radial bore defined in an end portion of the adjustment sleeve 22. In some embodiments, the sleeve fastener 24 and the sleeve fastener washer 46 are integrally connected.

An adjustment mechanism 26 is rotatably coupled to an end portion of the adjustment sleeve 22 and threadably connected to a threaded elongated member 28 through the adjustment mechanism aperture 60. The adjustment mechanism 26 adjusts longitudinally the threaded elongated member 28 to adjust the overall end-to-end length of the connecting rod 10 in a gradual manner. The adjustment sleeve 22 includes a slot 23, through which one can observe the longitudinal position of an end portion 29 of the threaded elongated member 28 relative to the adjustment sleeve 22. As such, one can determine the amount longitudinal adjustment that was made.

The threaded elongated member 28 includes a second ball joint 30. The second ball joint 30 includes a second ball joint cage 32 adapted to fit a second ball member 34. The second ball member 34 passes through a second ball joint aperture 50 that is sized and proportioned to fit the second ball member 34. A second ball stud 36 secures the second ball member 34 to an external fixator ring or other external supports (not shown). The second ball joint cage 32 allows angular and rotational alignment of the external fixation strut 10 relative to the second ball member 34.

Figure 3B:
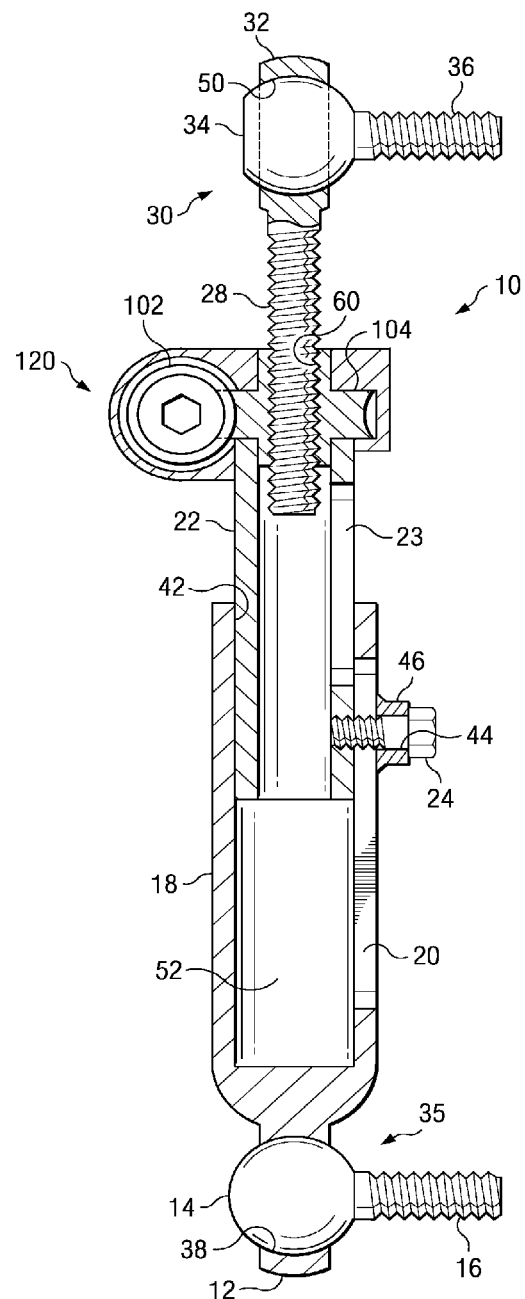
FIG. 3B is a cutaway view of another embodiment of an external fixation strut of the present disclosure.

FIG. 3B is a cutaway view of another embodiment of the external fixation strut of the present disclosure for an external fixation device. This embodiment is similar to the embodiment shown in FIG. 3A, except that the adjustment mechanism 26 is replaced by a gear-based adjustment mechanism 100. As shown in FIG. 3C, which is a focused, perspective view of the embodiment shown in FIG. 3B, the gear-based adjustment mechanism 100 includes a worm gear 102 disposed in a orthogonal orientation relative to the threaded elongated member 28, and a connecting gear 104 coupling the worm gear 102 and the threaded elongated member 28. The connecting gear 104 has a central opening defined therethrough and teeth 106. The central opening of the connecting gear allows a portion of the threaded elongated member 28 to pass through while the teeth 106 of the same engages the thread of the worm gear 104, thereby coupling the worm gear 102 and the threaded elongated member 28. As such, longitudinal adjustment of the threaded elongated member 28 is effected by the rotation of the worm gear 104.

It is to be appreciated that adjustment mechanisms suitable for the embodiments in the present disclosure are not limited to thumbwheel-based and gear-based adjustment mechanisms that have been discussed. Any adjustment mechanisms known in the art can be incorporated into the embodiments disclosed herein. For example, electrical connections can be incorporated into any of the embodiments discussed herein for strut adjustment by a motorized wrench as disclosed in U.S. Provisional Application No. 61/029,483, which is incorporated herein by reference.

In embodiments in which an electrical wrench is used to make the strut adjustment. The adjustment tool may include a rotational shaft encoder or other feedback sensor that counts the number of turns of the rotating shaft of the tool. The adjustment tool may further include a magnetic feedback sensor communicating with magnetic ring transmitter located on the adjustment mechanism of the external fixator strut that counts the number of turns of the adjustment mechanism of the external fixator strut.

Some exemplary embodiments may include a digital ruler or feedback sensor to determine the overall length and/or length adjustment amount of the external fixator strut. For determining the resistance during the adjustment of the external fixator strut, some exemplary embodiments may include a feedback torque measurement sensor to monitor resistance during the adjustments of the external fixator strut and provide a turning profile.

In addition to or instead of the displays, an electrical sensor may be provided which generates a signal when the specified target adjustment is obtained. A display can be mechanically activated in a conventional manner, e.g., by an axially movable pin, a pivotably movably mounted bar, etc. Additionally or alternatively, an electrical sensor can be used in a conventional manner to generate a signal when the specified target adjustment is obtained. Signals from the electronic sensor are evaluated in a known manner by an electronic circuit in order to trigger conventional acoustic or optical devices when the target torque is obtained.

FIG. 4A is a perspective view of one embodiment of the external fixation strut of the present disclosure. The external fixation strut 10 includes a first ball joint cage 12 that houses a first ball member 14. The first ball member 14 includes a first ball stud 16 that extends through the first ball joint cage 12 and is operable to secure the first ball member 14 to an external fixator ring or other external supports (not shown). The first ball joint cage 12 allows angular (rotational) movements of the external fixation strut in three orthogonal planes in directions X1, Y1 and Z1 relative to first ball member 14. These movements allow the first ball joint cage 12 to be secured at different angles relative to an external fixator ring or other external supports (not shown).

A telescoping strut housing 18 extends longitudinally from the first ball joint cage 12 and has an aperture (not shown) extending longitudinally from the first ball joint cage 12. The telescoping strut housing 18 includes a telescoping housing adjustment aperture 20. An adjustment sleeve 22 is positioned in the axial bore (not shown) of the telescoping strut housing 18. The movement of the adjustment sleeve 22 in the axial bore (not shown) of the telescoping strut housing 18 allows for an adjustment to the distance "B," which in turn leads to a coarse adjustment to the end-to-end length "A" of the external fixation strut 10 in a rapid manner.

The adjustment sleeve 22 includes a sleeve fastener 24 disposed through a sleeve fastener washer 46 and the telescoping housing adjustment aperture 20 to secure the adjustment sleeve 22 to the telescoping strut housing 18. The telescoping housing adjustment aperture 20 also serves as a window to allow positioning and referencing of the adjustment sleeve 22 and/or the threaded elongated member 28 to aid in the adjustment of the end-to-end length "A" of the external fixation strut 10.

An adjustment mechanism 26 is rotatably coupled to an end portion of the adjustment sleeve 22 and threadably connected to a threaded elongated member 28. The adjustment mechanism 26 may be rotated to engage the threads of the threaded elongated member 28, which would adjust longitudinally the distance "C" and adjust the end-to-end length "A" of the external fixation strut 10 in a gradual manner. The adjustment sleeve 22 includes a slot 23, through which one can observe the longitudinal position of an end portion 29 of the threaded elongated member 28 relative to the adjustment sleeve 22. As such, one can determine the amount longitudinal adjustment that was made.

The threaded elongated member 28 includes a second ball joint 30 that includes a second ball joint cage 32 adapted to fit a second ball member 34. The second ball member 34 includes a second ball stud 36 that passes through the second ball joint cage 32 and is operable to secure the second ball joint 30 to an external fixator ring or other external supports (not shown).

The second ball joint cage 32 may be rotated in three orthogonal planes in directions X2, Y2 and Z2 relative to second ball member 34. This movement allows the second ball joint cage 32 to be secured at different angles relative to an external fixator ring or other external supports (not shown). It is to be appreciated that the first ball joint cage 12 of the external fixation strut may be but does not have to be oriented at the same angle, position or face relative to the second ball joint cage 32.

Graduation marks 74 are defined in or formed on the adjustment sleeve 22 and telescoping strut housing 18. The graduation marks 74 are disposed proximate to the slot 23 and telescoping housing adjustment aperture 20 and may be calibrated into discrete increments (e.g., one millimeter increments) to indicate the distance between the first ball joint cage 12 and the second ball joint 30, which correspond to the end-to-end length "A" of the external fixation strut 10.

The graduation marks 74 indicate the lengths of the external fixation strut 10 as a relative value, rather than the distance from some predetermined specific length. The graduation marks do not necessarily have to be based on a traditional measuring system, or indicate the effective length of the strut at all. For instance, the graduation marks could indicate the percentage of total rod extension, or daily increments for cases where the translation takes place over an extended period of time. Reference to a neutral position can be useful to set the base members at a predetermined "neutral" position.

It is to be appreciated that in some embodiments, it may be desirable to limit the axial rotations $X_1$ and $X_2$ of the external fixation strut relative to the first and second balls 14 and 34. For example, as discussed above, strut length adjustments are effected by the rotation of adjustment mechanism 26 relative to a threaded elongated member 28 that is not operable to rotate axially. If the threaded elongated member 28 is operable to freely rotate about its longitudinal axis, the desired strut length adjustment cannot be precisely effected. To ensure precise strut length adjustment, it is desirable to limit the axial rotations $X_1$ and $X_2$ of the external fixation strut relative to the first and second ball members 14 and 34. FIG. 4B is a perspective view of a portion of an external fixation strut that has only 2 degrees of rotational freedom ($Y_2$ and $Z_2$) relative to the first and second balls 14 and 34. The second ball joint cage 32 in FIG. 4B has a pair of bores (not shown) defined therethrough at opposing peripheral portions, and the pair of bores are operable to receive a pair of pins 110. The pair of pins 110 extends partially into a radial groove 112 defined in the second ball member 34. As such, the pair of pins 110 allows the external fixation strut to rotate about a first axis defined by the pins 110 and a second axis that is orthogonal the plane define by the groove 112. The pair of pins 110, however, prevent the external fixation strut to rotate about a third axis that is orthogonal to the first and second axes. Although not shown in FIG. 4B, the first ball joint cage and the first ball member 14 are similarly configured to include a pair of pins 110 to limit the axial rotation of the external fixation strut relative to the first ball member 14. It is to be appreciated that in some embodiments, one pin 110, rather than a pair of pins 110 is sufficient to eliminate the undesirable third degree of rotational freedom.

Figure 5A:
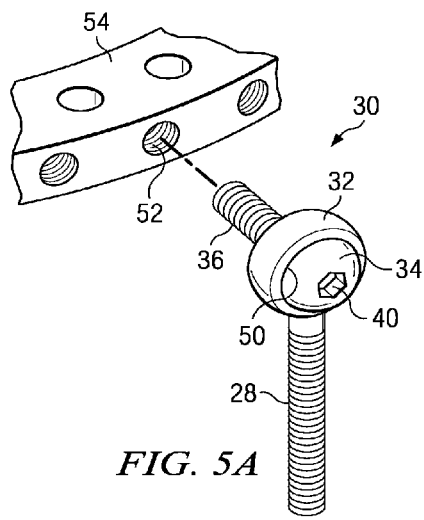
FIGS. 5A, 5B, 5C and 5D are perspective views of portions of embodiments of an external fixation strut of the present disclosure.

FIG. 5A is a perspective view of a portion of one embodiment of an external fixation strut of the present disclosure. The second ball joint 30 includes a second ball joint cage 32 adapted to fit a second ball member 34. The second ball member 34 passes through a second ball joint aperture 50 that is sized and proportioned to fit the second ball member 34. A second ball joint cage 32 includes a second ball joint cage stud 36 that is operable to be inserted through a threaded aperture 52 on an outer surface of an external fixator ring 54 or other second external support to secure the second ball joint 30 to an outer surface of an external fixator ring or other external support. The second ball joint 30 is connected to a threaded elongated member 28. The second ball stud 36 as well as the second ball member 34 may have one or more additional slots 40 or nuts (not shown) operably connected thereto to tighten and lock the stud or ball in the desired positions. The slots 40 may use any type head fastener known to the skilled artisan, e.g., slotted, Phillips, hex, socket, high-torque or other fastener/head.

It is to be appreciated that the configuration of the second ball stud 36 may be varied to accommodate various designs of the apertures in the external fixator ring 54 and to improve the ease of connecting the second ball stud 36 to the external fixator ring 54.

Figure 5B:
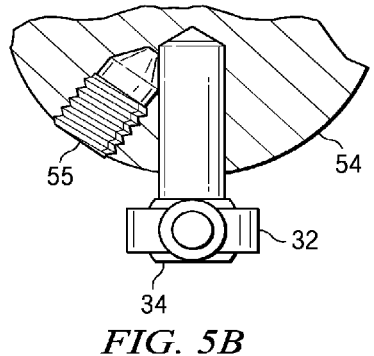

FIG. 5B is a cutaway view of a portion of another embodiment of an external fixation strut of the present disclosure. In this embodiment, the second ball stud 36 has a smooth outer surface. The second ball stud 36 is operable to be received in an aperture 53, which has an smooth inner surface, and substantially locked in place by a set screw 55 inserted into aperture 57 of the external fixator ring 54. The aperture 53 is aligned at an angle that substantially corresponds to the shape of the angled tip of the set screw 31, thereby increasing the contact area between the second ball studs 36 and the set screw 55.

Dynamic loading on the contact surface between the second ball stud 36 and the set screw 55 can cause the contact surface to deform and ultimately cause the second ball studs 36 to become loosened. Thus, the second ball studs 36 can be configured to have grooves defined therein to allow for optimal gripping and to accommodate for the dynamic loading of the contact surface.

Figure 5C:
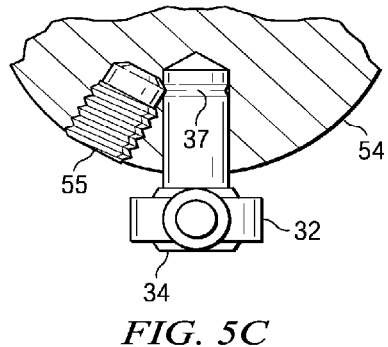
Figure 5D:
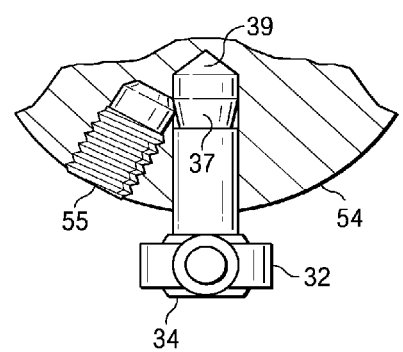

FIG. 5C is a cutaway view of a portion of another embodiment of an external fixation strut of the present disclosure. In this embodiment, the second ball stud 36 has a smooth outer surface and includes a circumferential groove 37. FIG. 5D is a cutaway view of a portion of yet another embodiment of an external fixation strut of the present disclosure. In this embodiment, the second ball stud 36 has a smooth outer surface and includes a circumferential groove 37 and a conical tip 39. The second ball stud 36 is operable to be received in an aperture 53, which has an smooth inner surface, and substantially locked in place by a set screw 55 inserted into aperture 57 of the external fixator ring 54. The conical tip 39 allows for better guidance for the insertion of the second ball stud 36 and increased contact surface between the second ball stud 36 and the inner surface of the aperture 53 for improved stability. In addition, the inclusion of a conical tip 39 increases the effective length of the second ball stud 36 and further improves the stability of the second ball stud 36 in the aperture 53. It is to be appreciated that, although not shown in FIGS. 5A-D, the first ball joint 35 and the first ball member 14 can be similarly configured as discussed in FIGS. 5A-D.

FIGS. 6A and 6B are a perspective view and a cross sectional view of a ball joint lockable by a split ball joint cage, respectively. The ball joint 30 includes a split ball joint cage 32 configured to receive a ball 34. The split ball joint cage 32 is divided into upper and lower portions 32a and 32b that substantially encapsulate the ball 34. The upper portion 32a includes bores 54a and 54b defined therethrough, and the low portion 32b includes corresponding threaded apertures (not shown) defined therein operable to receive fasteners 56a and 56b that are inserted through bores 54a and 54b. The fasteners 56a and 56b secure the ball 34 within the split ball joint cage 32a and 32b and limit the motion of the ball 34. The ball 34 passes through a ball joint aperture 50 that is sized and proportioned to fit the ball 34. A ball stud 36 is operable to secure the ball 34 to an external fixator ring or other external supports (not shown). The split ball joint cage 32a is connected to a threaded elongated member 28 and allows angular and rotational alignment of the external fixation strut (not shown) relative to the ball 34.

Shown in FIG. 6C is another embodiment of a ball joint lockable by a partially split ball joint cage. The ball joint 30 includes a partially split ball joint cage 32 adapted to fit a ball 34. The partially split ball joint cage 32 includes a gap 120 defined therethrough, and the gap 120 partially splits the ball joint cage 32 into first and second split portions 122 and 124. The first split portion includes a bore 54a defined therethrough, and the second portion includes a threaded aperture (not shown) that is operable to receive a fastener 56a that is inserted through the bore 54a. The ball 34 passes through a ball joint aperture 50 that is sized and proportioned to fit the ball 34, and the fastener 54a secures the ball 34 within the partially split ball joint cage 32 and limit the motion of the ball 34.

Figure 7:
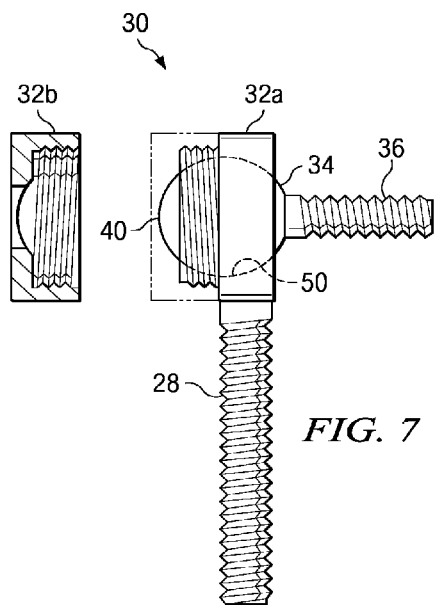
FIG. 7 is a perspective view of a ball joint lockable by a threaded ball joint cage cup.

FIG. 7 is a perspective view of a ball joint lockable by a threaded ball joint cage cap. The threaded ball joint 30 includes a ball cage having a first threaded portion 32a and a threaded locking member 32b operable to engage the surface of a threaded ball member 34. The threaded ball joint cages 32a and 32b are operable to be coupled to hold the ball 34 therein. The first threaded portion 32a is operable to mate with a threaded portion of the threaded locking member 32b to limit the motion of the threaded ball 34. The ball 34 passes through a threaded ball joint aperture 50 that is sized and proportioned to fit the threaded ball 34. A threaded ball stud 36 is operable to secure the threaded ball 34 to an external fixator ring or other external supports (not shown). The threaded ball joint cage 32 is connected to a threaded elongated member 28 and allows angular and rotational alignment of the external fixation strut (not shown) relative to the ball 34.

Figure 8:
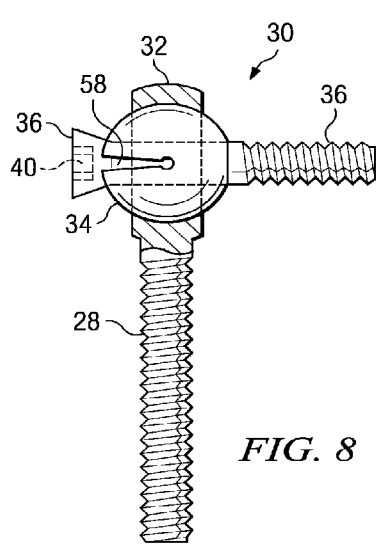
FIG. 8 is a perspective view of a ball joint lockable by split ball.

FIG. 8 is a perspective view of a ball joint lockable by split ball. In FIG. 8, the split ball joint 30 includes a ball joint cage 32 adapted to fit a split ball 34. The split ball 34 includes an aperture 58 defined therethrough, and the aperture 58 allows a split ball stud 36 to be inserted through the split ball 34. The split ball stud 36 has a threaded end portion and a smooth intermediate portion such that when the split ball stud 36 is inserted through the aperture 58, the intermediate portion expands the aperture 58. The expansive force exerted on the walls of the aperture 58 frictionally secures the ball 34 and cage 32 in the desired positions. The threaded end of the threaded ball stud 36 is operable to secure the split ball 34 to an external fixator ring or other external supports (not shown). The split ball joint cage 32 is connected to a threaded elongated member 28 and allows angular and rotational alignment of the external fixation strut (not shown) relative to the ball 34.

Figure 9:
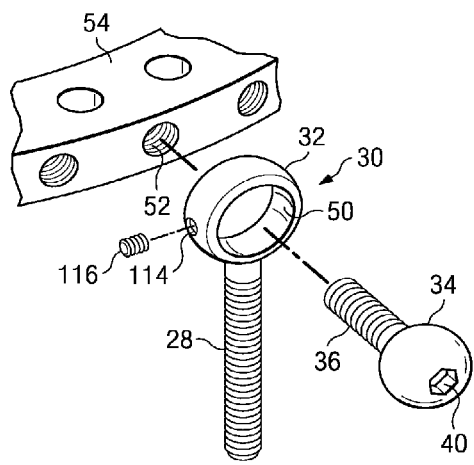
FIG. 9 is an exploded view of a ball joint lockable by a set screw.

FIG. 9 is a perspective view of a ball joint lockable by a set screw. In FIG. 9, the ball joint cage 32 includes a threaded radial bore 114 defined therethrough and a set screw 116 inserted through the threaded radial bore 114. The tip of the set screw 116 exerts a frictional force on the second ball member 34 to fix the second ball member 34 in one orientation. In some embodiments, the ball joint cage 32 may be configured to receive additional set screws 116 to increase the total frictional force on the second ball member 34.

Figure 10:
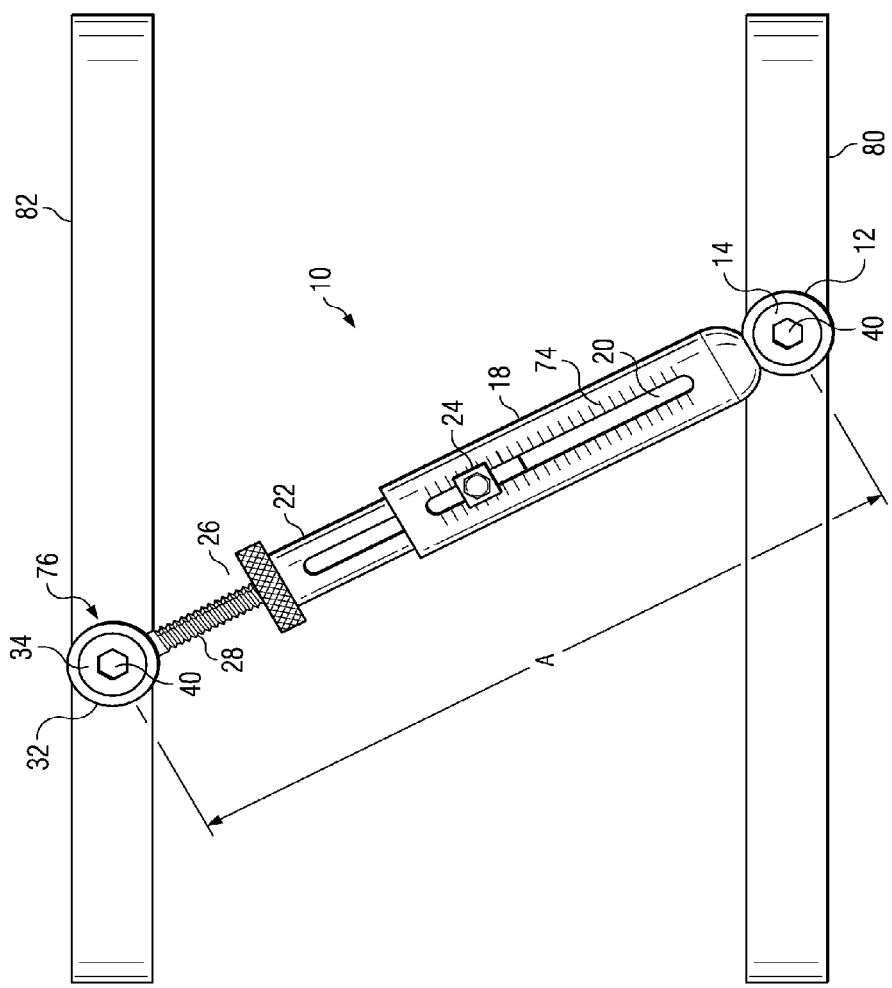
FIG. 10 is a side view of one embodiment of the external fixation strut of the present disclosure attached to the outer surface of an external fixation device.

FIG. 10 is a side view of one embodiment of the external fixation strut of the present disclosure attached to an external fixation device. An external fixation strut 10 is connected between a first external fixator ring 80 and a second external fixator ring 82. FIG. 10 depicts a single external fixation strut 10 disposed between the first external fixator ring 80 and the second external fixator ring 82 for simplicity sake. The skilled artisan will readily understand that numerous (e.g., 4, 6, or 8) external fixation struts 10 may be attached at various positions about the external fixator rings, that the angle of the external fixation strut 10 relative to the first external fixator ring 80 and the second external fixator ring 82 may be varied, and that the length of the external fixation strut 10 may be varied and adjusted.

A first ball joint cage 12 is secured to the external fixator ring 80 or other external supports. The external fixation strut 10 includes a first ball joint cage 12 that houses a first ball member 14. The first ball member 14 includes a first ball stud 16 that passes through an aperture (not shown) in the first external fixator ring 80 to secure the first ball member 14 to the external fixator ring 80 or other external supports. The first ball joint cage 12 allows angular and rotational alignment of the external fixation strut relative to first ball member 14. This movement allows the first ball joint cage 12 to be secured at different angles relative to the first external fixator ring 80 or other first external support.

A telescoping strut housing 18 extends from the first ball joint cage 12 and has an aperture (not shown) extending longitudinally from the first ball joint cage 12. The telescoping strut housing 18 includes a telescoping housing adjustment aperture 20 defined therethrough. An adjustment sleeve 22 is positioned in the axial bore (not shown) of the telescoping strut housing 18. The adjustment sleeve 22 is slidable within the bore (not shown) to allow adjustment of the coarse end-to-end length "A" of the external fixation strut 10 in a rapid manner. The movement of the adjustment sleeve 22 in the axial bore (not shown) of the telescoping strut housing 18 allows the distance to be changed and in turn change the end-to-end length of the external fixation strut 10.

The adjustment sleeve 22 includes a sleeve fastener 24 positioned through the telescoping housing adjustment aperture 20 to secure the adjustment sleeve 22 to the telescoping strut housing 18. The telescoping housing adjustment aperture 20 also serves as a window to allow positioning and referencing of the adjustment sleeve 22 and or the threaded elongated member 28 to aid in the adjustment of the end-to-end length of the external fixation strut 10. The graduation marks 74 indicate the lengths of the external fixation strut 10 as a relative value, rather than the distance from some predetermined specific length. The graduation marks do not necessarily have to be based on a traditional measuring system, or indicate the effective length of the strut at all. For instance, the graduation marks could indicate the percentage of total rod extension, or daily increments for cases where the translation takes place over an extended period of time. Reference to a neutral position can be useful to set the base members at a predetermined "neutral" position.

An adjustment mechanism 26 is rotatably coupled to an end portion of the adjustment sleeve 22 and threadably connected to a threaded elongated member 28. The adjustment mechanism 26 may be rotated to engage the threads of the threaded elongated member 28 and thereby adjust longitudinally the end-to-end length "A" of the external fixation strut 10 in a gradual manner. The threaded elongated member 28 includes a second ball joint 30 with a second ball joint cage 32 adapted to fit a second ball member 34. The second ball member 34 includes a second ball stud 36 that passes through an aperture (not shown) in the second external fixator ring 82 to secure the second ball joint 30 to an external fixator ring 82 or other second external support.

The second ball joint cage 32 allows angular and rotational alignment of the external fixation strut 10 relative to second ball member 34. This movement allows the second ball joint cage 32 to be secured at different angles relative to the second external fixator ring 82 or other second external support.

Figure 11:
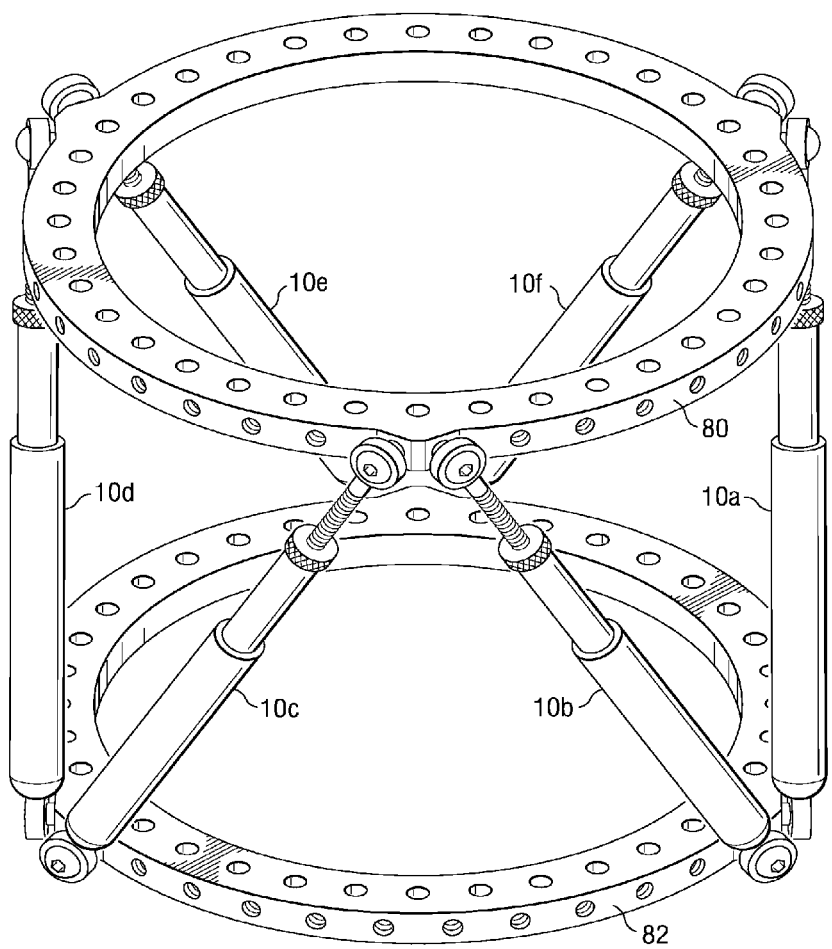
FIG. 11 is a side view of one embodiment of six external fixation struts of the present disclosure attached to the outer surface of an external fixation device.

FIG. 11 is a perspective view of one embodiment of the external fixation device having 6 connecting rods to immobilize bone segments. The external fixation device includes a first external fixator ring 80 and a second external fixator ring 82 that surround a bone (not shown). The first external fixator ring 80 and a second external fixator ring 82 are connected by 6 external fixation struts 10a-10f. Each of the external fixation struts (10a, 10b, 10c, 10d, 10e, and 10f) includes a first articulatable ball joint (not shown) that houses a first ball (not shown). The first ball (not shown) includes a first ball stud (not shown) that passes through a slot (not shown) into a threaded aperture in the external fixator ring 80.

Since there are multiple external fixator struts, it is desirable to be able to uniquely identify each strut so that the strut length adjustments for each strut can be tracked and implemented. An information indicator may be mounted onto or embedded into the struts for identifying the struts. In some embodiments, the information indicator may be a physical identifier, such as inscription, paper, or label of a code, color, or serial number corresponding to relevant information. Examples of the relevant information embodied or represented by the information indicator may include the type of the strut, the maximum or minimum strut length, strut number, etc. In some embodiments, the information indicator may be an electronic identifier. One common method of identification includes a radiofrequency (RF) sensor that wirelessly communicates with a radio frequency transmitter (RFID) located on the adjustment mechanism of the external fixator strut. Another strut number identifier may include a bar code reader that counts a specific number of grooves on the adjustment mechanism of the external fixator strut or communicates with magnetic strip located on the adjustment mechanism of the external fixator strut. In another embodiment, strut number identifier includes a sensor that receives information from a touch memory button located on the adjustment mechanism of the external fixator strut. Another embodiment of the present invention provides that the strut number is determined manually and allow the tool to engage the adjustment mechanism and rotates the adjustment mechanism on the desired number of turns. In other embodiments, the information indicator may be any other device suitable to embody or represent information or a combination of the types of indicators discussed in the present application.

A telescoping strut housing (not shown) extends from the first articulatable joint (not shown) to an adjustment sleeve (not shown) and threaded elongated member (not shown) to a second ball. The second ball (not shown) includes a second ball stud (not shown) that passes into a threaded aperture of the external fixator ring or other fixation device 82.

The methods of the present disclosure may be performed with a subject, e.g., a human or another vertebrate animal. One or more bones (of the subject) to be fixed may be selected. Any suitable bone(s) may be selected, such as a long bone(s) and/or at least a pair of bones connected via an anatomical joint. Exemplary bones include leg bones (femur, tibia, and fibula), arm bones (humerus, radius, and ulna), foot bones (calcaneus, talus, metatarsals, and phalanges), wrist/hand bones (carpals, metacarpals, and phalanges), etc. In exemplary embodiments, one or more bones including at least one long bone may be selected.

An external fixation device may be constructed along and at least partially around the selected bone(s). The external fixation device may include a plurality of rings fixed in position relative to one another by numerous external fixation struts secured to the rings.

The external fixation device may be connected to the selected bone(s). Connection may be performed at any suitable time, such as before, during, and/or after construction of the external fixation device. For example, the external fixation device may be assembled and then connected to bone, or individual external fixation device members or external fixation device sub-assemblies may be connected to the bone before the external fixation device is fully assembled. Connection of the external fixation device to bone may include placing connectors, such as wires, pins, screw, and/or rods, among others, through the skin and into, through, and/or around the selected bone.

The external fixation device may be reconfigured while it is connected to the one or more selected bones. Reconfiguration may include adjusting the length, angle, position, and/or connection site of one or more external fixation device components, particularly external fixation struts. In some embodiments, reconfiguration may involve lengthening and/or shortening one or more (or all) external fixation struts of the external fixation device. In some embodiments, reconfiguration may involve replacing one or more external fixation struts with a different connecting rod(s). The different connecting rod may be of different size, pivotability, adjustability, shape, and/or the like.

The external fixation device may be braced to facilitate reconfiguration. Bracing the external fixation device may stiffen and/or stabilize the external fixation device such that reconfiguration produces fewer undesired changes to the external fixation device structure as the external fixation device is weakened and altered during reconfiguration. Bracing may be performed by securing at least one brace to the external support. In some examples, the brace may be configured to be clipped onto the external fixation device members before the brace is fully secured to the external fixation device members. For example, the brace may include one or more external fixation device engagement elements that are biased to opposingly engage one or more respective external fixation device members. In any case, each engagement element may be secured in place on the external fixation device member by operating a user control, manually or with a tool. Furthermore, the relative spacing and angular disposition of the engagement elements may be fixed by operating a user control, either the same user control(s) for securing the engagement element to a frame member or a distinct user control.

In some examples, the brace may include one or more movable joints, and the brace may be installed in engagement with the external fixation device members with one or more of the joints in a movable configuration. The movable joints then may be adjusted to a locked (fixed) configuration. Alternatively, or in addition, the brace may include a plurality of movable joints and one or more of the movable joints may be locked before or during brace placement onto the frame, and one or more other of the movable joints may be locked after brace placement onto the external fixation device.

The brace may be removed after frame reconfiguration. Accordingly, the brace may be installed with the frame (and connecting rod) fixing bone and removed with the frame reconfigured and still fixing bone. The brace thus may be present on the external fixation device for only a fraction of the time that the external fixation device is fixing bone.

It is contemplated that any embodiment discussed in this specification can be implemented with respect to any method, kit, reagent, or composition of the disclosure, and vice versa. Furthermore, compositions of the disclosure can be used to achieve methods of the disclosure.

It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An external fixation strut having a longitudinal axis defined therein, the fixation strut comprising:
 a strut housing having an axial bore defined therethrough;
 a first ball joint coupled to an end portion of the strut housing, the first ball joint including a first ball joint cage and a first ball member, the first ball member being rotatably coupled to the first ball joint cage, the first ball joint cage including a bore defined therethrough, and the first ball member including a circumferential groove defined therein;
 a pin inserted through the bore of the first ball joint cage and at least partially into the circumferential groove of the first ball member to at least partially limit rotation of the first ball member relative to the first ball joint cage;
 an adjustment sleeve slidably disposed within the axial bore, the adjustment sleeve and the strut housing being releasably coupled by a connector;
 an elongated member;
 a second ball joint coupled to an end portion of the elongated member; and
 an adjustment mechanism having a bore defined therethrough, the elongated member being disposed through the bore, the adjustment mechanism being operable to adjust a longitudinal position of the elongated member relative to the adjustment sleeve.

2. The external fixation strut of claim 1, wherein
 the strut housing includes an aperture defined in a wall of the strut housing,
 the aperture extends longitudinally along the strut housing,
 the adjustment sleeve includes a radial bore, and
 the connector includes a screw disposed through the aperture of the strut housing and received in the radial bore.

3. The external fixation strut of claim 2, wherein
 the connector includes a washer having a central opening defined therein,
 the washer is disposed on an outer surface of the strut housing, and
 the screw is disposed through the central opening of the washer, through the aperture of the strut housing, and received in the radial bore.

4. The external fixation strut of claim 1, wherein
 the first ball joint includes a first ball stud extending outwardly from the first ball member, and
 the first ball stud is operable to be received in an aperture in a first external support member.

5. The external fixation strut of claim 4, wherein the second ball joint includes
 a second ball joint cage;
 a second ball member rotatably coupled to the second ball joint cage; and
 a second ball stud extending outwardly from the second ball member, the second ball stud being operable to be received in an aperture in a second external support member.

6. The external fixation strut of claim 4, wherein the first ball stud includes an end portion.

7. The external fixation strut of claim 4, wherein the first ball stud includes a smooth outer surface, a circumferential groove defined in the outer surface, and a conical tip.

8. The external fixation strut of claim 4, wherein an orientation of the first ball member relative to the first ball joint cage is operable to be substantially fixed.

9. The external fixation strut of claim 8, wherein
 the first ball joint cage includes a radial gap defined therethrough,
 the radial gap partially splits the first ball joint cage into first and second split portions,
 the first split portion includes a first aperture defined therethrough,
 the second split portion includes a second aperture defined therethrough, and
 the first and second apertures are operable to receive a fastener.

10. The external fixation strut of claim 8, wherein
 the first ball member includes an aperture defined therethrough,
 the aperture is operable to receive a split ball stud disposed through the aperture,
 the split ball stud includes an end portion and a flared end portion operable to expand the aperture when the split ball stud is inserted through the aperture.

11. The external fixation strut of claim 8, wherein the first ball joint cage includes a first portion and a locking member operable to engage a surface of the first ball member such that when the locking member is engaged with the first portion the movement of the first ball member is substantially limited.

12. The external fixation strut of claim 8, wherein
 the first ball joint cage includes a radial bore,
 a locking screw is disposed through the radial bore of the first ball joint cage,
 an end portion of the locking screw exerts a frictional force on the first ball member such that movement of the first ball member is substantially limited.

13. The external fixation strut of claim 1, wherein the adjustment sleeve includes a longitudinally extending slot defined therethrough.

14. The external fixation strut of claim 1, wherein the adjustment mechanism includes a locking mechanism.

15. The external fixation strut of claim 1, further comprising an information indicator coupled to the adjustment sleeve or the strut housing.

16. The external fixation strut of claim 15, wherein the information indicator includes an electronic information identifier.

17. The external fixation strut of claim 1, further comprising a device for electronically identifying a strut.

18. The external fixation strut of claim 1, further comprising an electronic device for monitoring strut adjustments.

19. An external fixation strut comprising:
 a strut housing having an axial bore defined therethrough and an aperture defined in a wall of the strut housing, the aperture extending longitudinally along the strut housing;
 an adjustment sleeve slidably disposed within the axial bore, the adjustment sleeve and the strut housing being releasably coupled by a connector, the adjustment sleeve including a radial bore, and the connector including a screw disposed through the aperture of the strut housing and received in the radial bore;
 an elongated member;
 a first ball joint coupled to an end portion of the strut housing, the first ball joint including
  a first ball joint cage including a bore defined therethrough;
  a first ball member rotatably coupled to the first ball joint cage and including a circumferential groove defined therein;
  a pin inserted through the bore of the first ball joint cage and at least partially into the circumferential groove of the first ball member to at least partially limit rotation of the first ball member relative to the first ball joint cage; and a first ball stud extending outwardly from the first ball member, the first ball stud being operable to be received in a ring aperture in an outer or inner surface of a first external fixator ring;

a second ball joint coupled to an end portion of the elongated member; and an adjustment mechanism that adjusts a longitudinal position of the elongated member relative to the adjustment sleeve.

20. A method of interconnecting first and second fixator rings with a strut, adjusting the strut to a pretreatment strut length, and making strut length adjustments during treatment, the rings each including a plurality of apertures defined in an inner or outer surface of the ring, the method comprising:

providing a first part of the strut, the first part including a first ball joint coupled to an end portion of a strut housing, the strut housing having an axial bore defined therethrough, the first ball joint including a first ball stud, a first ball joint cage and a first ball member, the first ball member being rotatably coupled to the first ball joint cage, the first ball joint cage including a bore disposed therethrough, and the first ball member including a circumferential groove defined therein;

inserting a pin through the bore of the first ball joint cage and at least partially into the circumferential groove of the first ball member to at least partially limit rotation of the first ball member relative to the first ball joint cage;

providing a second part of the strut, the second part including a second ball joint coupled to an end portion of an elongated member; the elongated member being coupled to an adjustment mechanism, the adjustment mechanism being coupled to an adjustment sleeve, and the second ball joint including a second ball stud;

disposing the adjustment sleeve within the axial bore of the strut housing;

connecting the first ball stud of the first ball joint to a first aperture of the first fixator ring;

connecting the second ball stud of the second ball joint to a second aperture of the second fixator ring;

positioning the adjustment sleeve relative to the strut housing to arrive at the pretreatment strut length;

releasably coupling the adjustment sleeve to the strut housing; and translating, using the adjustment mechanism, the elongated member to adjust the strut length.

21. The method of claim 20, wherein the first ball stud extends outwardly from the first ball member.

22. The method of claim 20, wherein the first ball joint cage includes a radial gap splitting the first ball joint cage into first and second split portions, the first split portion includes a first aperture defined therethrough, the second split portion includes a second aperture defined therein, the first and second apertures are operable to receive a fastener, the first ball stud extends outwardly from the first ball member, and the method further comprises inserting a fastener through the first aperture in the first split portion and into the second aperture thereby locking the first ball member in a spatial orientation by engaging an end portion of the fastener in the second aperture.

* * * * *